US007813470B2

(12) United States Patent
Kuwabara

(10) Patent No.: US 7,813,470 B2
(45) Date of Patent: Oct. 12, 2010

(54) THREE-DIMENSIONAL CONTENTS DETERMINATION METHOD USING TRANSMITTED X-RAY

(75) Inventor: Shoji Kuwabara, Ibaraki (JP)

(73) Assignee: Shimadzu Corporation, Kyoto (JP)

( * ) Notice: Subject to any disclaimer, the term of this patent is extended or adjusted under 35 U.S.C. 154(b) by 185 days.

(21) Appl. No.: 12/297,142

(22) PCT Filed: Dec. 4, 2006

(86) PCT No.: PCT/JP2006/324170

§ 371 (c)(1),
(2), (4) Date: Oct. 14, 2008

(87) PCT Pub. No.: WO2007/122770

PCT Pub. Date: Nov. 1, 2007

(65) Prior Publication Data

US 2010/0172470 A1 Jul. 8, 2010

(30) Foreign Application Priority Data

Apr. 13, 2006 (JP) ............................. 2006-111154

(51) Int. Cl.
*A61B 6/00* (2006.01)
(52) U.S. Cl. ............................. 378/4; 378/57
(58) Field of Classification Search .................. 378/4, 378/53, 54, 57
See application file for complete search history.

(56) References Cited

U.S. PATENT DOCUMENTS

| | | | | | |
|---|---|---|---|---|---|
| 4,888,693 | A | * | 12/1989 | Tam | .............................. 378/4 |
| 5,490,218 | A | * | 2/1996 | Krug et al. | .................. 382/100 |
| 2003/0016778 | A1 | * | 1/2003 | Tachizaki et al. | ............... 378/4 |
| 2006/0002504 | A1 | * | 1/2006 | De Man et al. | ................ 378/4 |
| 2006/0067461 | A1 | | 3/2006 | Yin et al. | |

FOREIGN PATENT DOCUMENTS

| | | | |
|---|---|---|---|
| JP | 63-266583 | A | 11/1988 |
| JP | 3-063556 | A | 3/1991 |
| JP | 03-185344 | A | 8/1991 |
| JP | 6-058288 | B2 | 8/1994 |
| JP | 6-242026 | A | 9/1994 |
| JP | 7-046080 | B2 | 5/1995 |
| JP | 7-104293 | B2 | 11/1995 |
| JP | 11-287643 | A | 10/1999 |
| JP | 2002-228603 | A | 8/2002 |
| JP | 2004-045212 | A | 2/2004 |
| JP | 2004-294233 | A | 10/2004 |

\* cited by examiner

*Primary Examiner*—Edward J Glick
*Assistant Examiner*—Alexander H Taningco
(74) *Attorney, Agent, or Firm*—Sughrue Mion, PLLC

(57) ABSTRACT

An X-ray that has passed through a target object 13 is detected by a two-dimensional X-ray detector 14 capable of energy discrimination, to determine an actual X-ray strength at a specific energy level. The target object 13 is rotationally scanned in predetermined angular steps around an axis perpendicular to the X-ray. The target object 13 is imaginarily divided into a large number of micro-sized unitary cubic cells, and each detection element 14a is considered to be receiving an X-ray that has passed through a plurality of unitary cubic cells. A data processor 6 creates a system of equations including a measured intensity ratio between the transmitted and direct X-rays and a theoretical X-ray intensity ratio calculated from the mass absorption coefficients, unknown weight ratios and density of the elements contained in each unitary cubic cell. The number of equations is equal to or larger than the total number of the elements having unknown weight ratios and the density. In this manner, one can measure the three-dimensional distribution of the weight ratio of each element and/or compound and the density in the target object containing a plurality of known kinds of elements and/or compounds.

5 Claims, 4 Drawing Sheets

THREE-DIMENSIONAL CONTENTS DETERMINATION METHOD USING TRANSMITTED X-RAY

CROSS REFERENCE TO RELATED APPLICATION

This application is a National Stage of International Application No. PCT/JP2006/324170 filed Dec. 4, 2006, claiming priority based on Japanese Patent Application No. 2006-111154, filed Apr. 13, 2006, the contents of all of which are incorporated herein by reference in their entirely.

TECHNICAL FIELD

The present invention relates to a three-dimensional contents determination method using a transmitted X-ray, for measuring a three-dimensional distribution of the weight ratios and density of a plurality of elements and/or compounds contained in an object to be measured (which is hereinafter called the "target object").

BACKGROUND ART

Nondestructive inspection systems and medical imaging apparatuses using a transmitted X-ray are conventionally known. For example, the nondestructive inspection system disclosed in Patent Document 1 measures the thickness of a target object located on or within a base member and made of a material different from that of the base member. In this system, the target object is irradiated with an X-ray whose wavelength is selected so that the peak of the entire spectrum of the X-ray is located near the absorption edge of the element of the target object, and the thickness of the target object is determined based on the intensity of a transmitted X-ray at the aforementioned wavelength near the absorption edge. More specifically, the intensity of the X-ray that has passed through the base member and target object is measured near the high-energy (short-wavelength) side of the absorption edge and also near the low-energy (long-wavelength) side of the absorption edge, and the thickness of the target object is calculated from the intensity values, the linear absorption coefficient of the target object near the high-energy side of the absorption edge and the linear absorption coefficient of the target object near the low-energy side of the absorption edge.

This conventional transmitted X-ray measurement method is basically designed on the premise that the target object is made of one kind of a known constituent (or element). Such a method is suited for some specific purposes, such as measuring the thickness of a specific heavy metal adhered to the inside of a pipe, closed container or similar structure. However, the method cannot be used if the target object is a mixture of two or more elements and/or compounds. Although Patent Document 1 also discloses a method for determining the content percentage of a specific element contained in an alloy object, the method only yields the content percentage of one specific element; it provides no information about the content percentage of the other elements. Another problem results from the use of a formula that utilizes the linear absorption coefficient, which represents the attenuation rate of an X-ray per unit length of material. Calculating the content percentage of a specific element by this formula leads to a rather inaccurate result since the formula does not take into account the influence of elements other than the specific one.

Currently, many people working in the industrial, medical or other fields have a strong demand for investigating the stereographic or three-dimensional distribution of elements or compounds contained in a target object. One of the conventionally known systems for obtaining a three-dimensional image by means of a transmitted X-ray is computer tomography (CT). These systems reproduce a three-dimensional image by illustrating the difference in the density of a substance inside a target object by shading or color variations. However, none of those systems can measure the three-dimensional concentration distribution of an element or compound contained in the target object.

Patent Document 1: Japanese Unexamined Patent Application Publication No. H11-287643

DISCLOSURE OF THE INVENTION

Problem to be Solved by the Invention

The present invention has been developed in view of these points, and its objective is to provide a three-dimensional contents determination method using a transmitted X-ray by which the three-dimensional distribution of the weight ratio of each of the elements and/or compounds contained in a target object and their density can be determined, given that the kind of each element or compound is previously known or presumable.

Means for Solving the Problems

To solve the aforementioned problem, a first aspect of the present invention provides a three-dimensional contents determination method using a transmitted X-ray, for determining a three-dimensional distribution of weight ratios and density of elements and/or compounds contained in a target object by means of an X-ray measurement system including:

an X-ray irradiator for irradiating the target object with a divergent X-ray or parallel pencils of X-rays having a predetermined energy range;

an X-ray detector with a two-dimensional array of micro-sized X-ray detection elements capable of energy discrimination for detecting a transmitted X-ray that has passed through the target object or a direct X-ray that has not passed through the target object;

a signal processor for obtaining X-ray intensity data of the transmitted or direct X-ray for each of the micro-sized X-ray detection elements on a basis of a detection signal produced by the X-ray detector; and a rotational scanner for rotating either the target object or the X-ray irradiator and the X-ray detector in steps of a predetermined rotation angle so that a relative position of the target object, the X-ray irradiator and the X-ray detector changes around an axis perpendicularly or obliquely intersecting with an incident X-ray impinging on the target object, the contents determination method comprising steps of:

imaginarily dividing the target object into a large number of three-dimensionally arranged unitary cubic cells, a size of the unitary cubic cell being determined by taking into account a difference between an incident area and exit area of the X-ray passing through the target object, a size of a detection surface of the micro-sized X-ray detection element, and a scan angle of the rotational scanner;

creating, for each rotational scan operation and each micro-sized X-ray detection element, a system of equations whose number is equal to or greater than a total number of elements and/or compounds having unknown weight ratios and the density in each of the aforementioned one or more unitary cubic cells including an equation including a measured intensity ratio between an intensity of the transmitted X-ray that has passed through the target object and an intensity of the direct X-ray that has not passed through the target object at a same energy level and a theoretical X-ray intensity ratio expressed using the mass absorption coefficients, the weight ratios and the density of all the elements and/or compounds contained in one or more unitary cubic cells located within a range where the X-ray passes through the target object, and an equation expressing that a sum of the weight ratios of the elements and/or compounds contained in one or more unitary cubic cells located within a range where the X-ray passes through the target object equals one; and detecting the transmitted X-ray that has passed through the target object and the direct X-ray that has not passed therethrough by means of the X-ray detector, calculating the measured intensity ratio from the X-ray intensity data thereby obtained, applying the measured intensity ratio to the system of equations, and solving the system of equations for the weight ratio of each element and/or compound and the density in each unitary cubic cell, thereby determining the three-dimensional distribution of the elements and/or compounds contained in the target object.

To solve the aforementioned problem, a second aspect of the present invention provides a three-dimensional contents determination method using a transmitted X-ray, for determining a three-dimensional distribution of weight ratios and density of elements and/or compounds contained in a target object by means of an X-ray measurement system including:

an X-ray irradiator for irradiating the target object with a divergent X-ray or parallel pencils of X-rays having a predetermined energy range;

an X-ray detector with a two-dimensional array of micro-sized X-ray detection elements capable of energy discrimination for detecting a transmitted X-ray that has passed through the target object;

a signal processor for obtaining X-ray intensity data of the transmitted X-ray for each of the micro-sized X-ray detection elements on a basis of a detection signal produced by the X-ray detector; and a rotational scanner for rotating either the target object or the X-ray irradiator and the X-ray detector in steps of a predetermined rotation angle so that a relative position of the target object, the X-ray irradiator and the X-ray detector changes around an axis perpendicularly or obliquely intersecting with an incident X-ray impinging on the target object, the contents determination method comprising steps of:

imaginarily dividing the target object into a large number of three-dimensionally arranged unitary cubic cells, a size of the unitary cubic cell being determined by taking into account a difference between an incident area and exit area of the X-ray passing through the target object, a size of a detection surface of the micro-sized X-ray detection element, and a scan angle of the rotational scanner;

in a case where all of the elements and/or the constituent elements of all of the compounds contained in the target object have absorption edges within an energy range that is measurable for a combination of the X-ray irradiator and the X-ray detector, creating, for each rotational scan operation and each micro-sized X-ray detection element, a system of equations whose number is equal to or greater than a total number of elements and/or compounds having unknown weight ratios and the density in each of the aforementioned one or more unitary cubic cells including an equation including a transmitted X-ray intensity ratio measured on both sides of the absorption edge of each element and a theoretical X-ray intensity ratio expressed using the mass absorption coefficients, the weight ratios and the density of all the elements and/or compounds contained in one or more unitary cubic cells located within a range where the X-ray passes through the target object, and an equation expressing that a sum of the weight ratios of the elements and/or compounds contained in one or more unitary cubic cells located within a range where the X-ray passes through the target object equals one; and detecting the transmitted X-ray that has passed through the target object by means of the X-ray detector, calculating the transmitted X-ray intensity ratio from the X-ray intensity data thereby obtained, applying the transmitted X-ray intensity ratio to the system of equations, and solving the system of equations for the weight ratio of each element and/or compound and the density in each unitary cubic cell, thereby determining the three-dimensional distribution of the elements and/or compounds contained in the target object.

To solve the aforementioned problem, a third aspect of the present invention provides a three-dimensional contents determination method using a transmitted X-ray, for determining a three-dimensional distribution of weight ratios and density of elements and/or compounds contained in a target object by means of an X-ray measurement system including:

an X-ray irradiator for irradiating the target object with a divergent X-ray or parallel pencils of X-rays having a predetermined energy range;

an X-ray detector with a two-dimensional array of micro-sized X-ray detection elements capable of energy discrimination for detecting a transmitted X-ray that has passed through the target object or a direct X-ray that has not passed through the target object;

a signal processor for obtaining X-ray intensity data of the transmitted or direct X-ray for each of the micro-sized X-ray detection elements on a basis of a detection signal produced by the X-ray detector; and a rotational scanner for rotating either the target object or the X-ray irradiator and the X-ray detector in steps of a predetermined rotation angle so that a relative position of the target object, the X-ray irradiator and the X-ray detector changes around an axis perpendicularly or obliquely intersecting with an incident X-ray impinging on the target object, the contents determination method comprising steps of:

imaginarily dividing the target object into a large number of three-dimensionally arranged unitary cubic cells, a size of the unitary cubic cell being determined by taking into account a difference between an incident area and exit area of the X-ray passing through the target object, a size of a detection surface of the micro-sized X-ray detection element, and a scan angle of the rotational scanner;

for each of the elements and/or compounds contained in the target object, if the element has an absorption edge within an energy range that is measurable for a combination of the X-ray irradiator and the X-ray detector, then, creating, for each rotational scan operation and each micro-sized X-ray detection element, a system of equations whose number is equal to or greater than a total number of elements and/or compounds having unknown weight ratios and the density in each of the aforementioned one or more unitary cubic cells including an equation including a transmitted X-ray intensity ratio measured on both sides of the absorption edge of each element and a theoretical X-ray intensity ratio expressed using the mass absorption coefficients, the weight ratios and the density of all the elements contained in one or more unitary cubic cells located within a range where the X-ray passes through the target object, and an equation expressing that a sum of the weight ratios of the elements and/or compounds contained in one or more unitary cubic cells located within a range where the X-ray passes through the target object equals one;

if the each element has no absorption edge within the measurable energy range, then, creating a system of equations whose number is equal to or greater than a total number of elements and/or compounds having unknown weight ratios and the density in each of the aforementioned one or more unitary cubic cells including an equation including a measured intensity ratio between an intensity of the transmitted X-ray that has passed through the target object and an intensity of the direct X-ray that has not passed through the target object at the same energy level, and a theoretical X-ray intensity ratio expressed using the mass absorption coefficients, the weight ratios and the density of all the elements contained in one or more unitary cubic cells located within a range where the X-ray passes through the target object, and an equation expressing that a sum of the weight ratios of the elements and/or compounds contained in one or more unitary cubic cells located within a range where the X-ray passes through the target object equals one; and detecting the transmitted X-ray that has passed through the target object by means of the X-ray detector, and also detecting the direct X-ray that has not passed through the target object by means of the X-ray detector, and calculating the transmitted X-ray intensity ratio or measured intensity ratio from the X-ray intensity data thereby obtained, applying the transmitted X-ray intensity ratio or measured intensity ratio to the system of equations, and solving the system of equations for the weight ratio of each element and/or compound and the density in each unitary cubic cell, thereby determining the three-dimensional distribution of the elements and/or compounds contained in the target object.

The divergent X-ray is a spreading X-ray beam emitted from a point-like or equivalently shaped X-ray irradiator with a predetermined solid angle. The parallel pencils of X-rays are a bundle of substantially parallel X-ray beams that are emitted from an X-ray irradiator having a flat shape or equivalent shape and scarcely spread.

EFFECT OF THE INVENTION

In any of the three-dimensional contents determination methods using a transmitted X-ray according to the first, second, or third aspect of the present invention, a detector having a two-dimensional array of micro-sized X-ray detection elements capable of energy discrimination is used as the X-ray detector so as to enable a two-dimensional measurement. Furthermore, rotating either the target object or the combination of the X-ray irradiator and X-ray detector adds one more dimension to the two-dimensional measurement to enable a three-dimensional measurement. The target object is modeled as a collection of a large number of micro-sized unitary cubic cells, in which the X-ray impinging on the target object passes through a plurality of unitary cubic cells before it exits from the opposite side and reaches the X-ray detector.

Based on this model, equations are created with unknowns including the weight ratios of the elements or compounds and their density in each unitary cubic cell. As the measured X-ray intensity, the first aspect of the present invention uses a measured intensity ratio between the transmitted X-ray that has passed through the target object and the direct X-ray that has not passed therethrough, the second aspect of the present invention uses an intensity ratio between the transmitted X-rays measured at energy levels before and after the absorption edge of each element, and the third aspect of the present invention switches the two types of X-ray intensity ratios according to whether or not the element concerned has an absorption edge.

Therefore, by the three-dimensional contents determination methods using a transmitted X-ray according to the first, second, or third aspect of the present invention, the three-dimensional distribution of the weight ratio of each of the elements and/or compounds and their density in the target object can be precisely obtained as long as the kinds of elements and/or compounds are previously known or presumable. Being capable of creating a precise three-dimensional image of, for example, the internal structure or composition of a target object in a non-destructive manner, the present techniques can be used in various fields, such as industrial inspection or medical diagnosis.

The three-dimensional contents determination method according to the first aspect of the present invention has a particularly wide range of applications, because it does not utilize the absorption edge and hence can determine the contents of almost all kinds of elements. The three-dimensional contents determination method according to the second aspect of the present invention is more accurate in contents determination, although the method can be used only for limited kinds of elements since it utilizes the absorption edge of each element.

EXPLANATION OF NUMERALS 1, 11, 21 . . . X-Ray Source
2, 12, 22 . . . X-Ray
3, 13 . . . Target Object
4 . . . X-Ray Detector
14 . . . Two-Dimensional X-Ray Detector
14a . . . Micro-Sized X-Ray Detection Element
15 . . . Sample Stage
16 . . . Scan Rotation Drive
21 . . . X-Ray Source
5 . . . Detection Signal Processor
51 . . . Preamp
52 . . . Proportional Amplifier
53 . . . Multi-channel Analyzer
6 . . . Data Processor
8 . . . Controller

BEST MODE FOR CARRYING OUT THE INVENTION

In advance of describing the three-dimensional contents determination method according to the present invention, a method for contents determination of an element or compound contained in a target object is hereinafter described with reference to the attached drawings. This method, which the present inventor previously proposed in Japanese Patent Application No. 2006-42407, forms the basis for the present invention. This method makes it possible to determine the average content and density of the entire target object or the two-dimensional distribution of the content and density averaged in the thickness direction.

Figure 1:
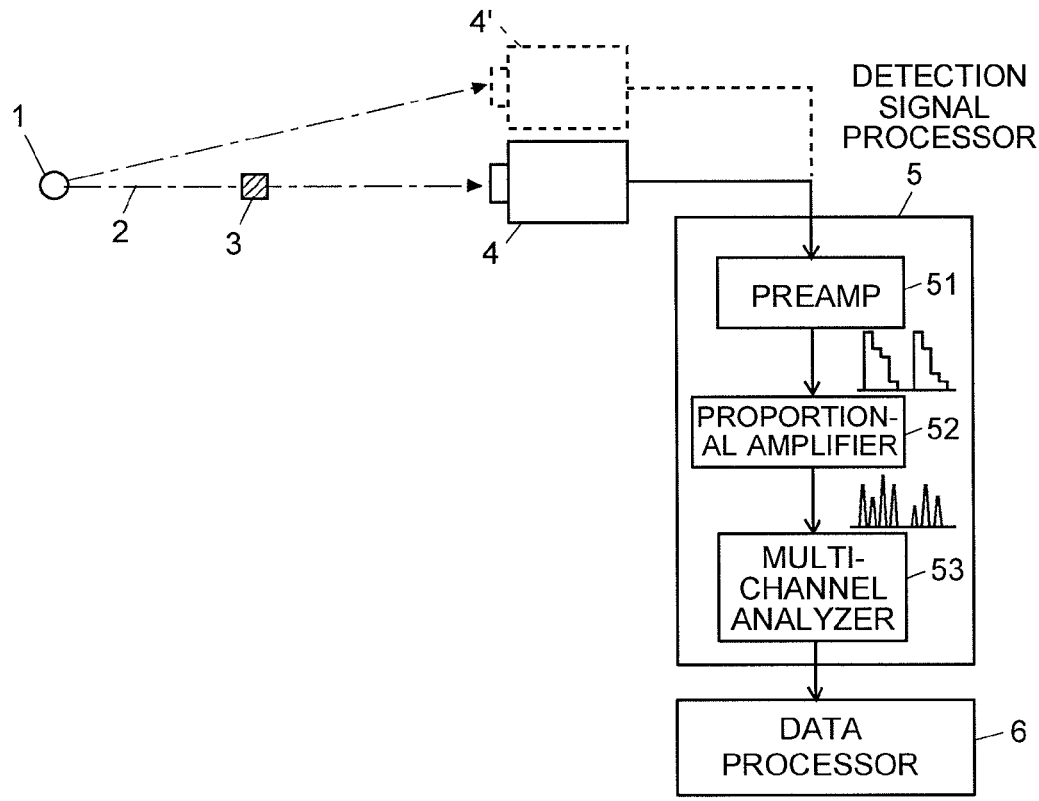
FIG. 1 is a schematic configuration diagram of a basic measurement system for the contents determination method according to the present invention.

FIG. 1 is a schematic configuration diagram of a basic measurement system for determining the average content and density of a target object. An X-ray 2 is emitted from an X-ray source 1 (e.g. an X-ray tube) and delivered onto a small target object 3. This X-ray passes through this target object 3 and reaches the X-ray detector 4. The X-ray source 1 can generate X-rays over a predetermined energy range and not at one specific wavelength, and the X-ray detector 4 can detect X-rays over the same energy range.

The X-ray detector 4 generates an electric signal corresponding to the energy of the incident X-ray. The detection signal is fed to a detection signal processor 5, which initially amplifies the signal by a preamp 51. The resultant signal is a pulse voltage signal in the form of steps, as shown in FIG. 1. The height of each step of this signal corresponds to the energy of each element contained in the target object 3. This pulse voltage signal is fed to a proportional amplifier 52 including a wave-shaping circuit, which changes the signal to appropriately-shaped pulses whose heights correspond to those of the aforementioned steps.

The multi-channel analyzer 53 discriminates the pulse signals on the basis of their pulse height, sorts them by different energy levels and counts the number of pulses for each energy level. The energy levels by which the signals are sorted by the multi-channel analyzer 53 can be externally set, and the analyzer sends the data processor 6 a value corresponding to the intensity of the transmitted X-ray at an arbitrary energy level. As will be described later, the data processor 6 performs calculations on the actual data of these X-ray intensity values to determine the weight ratio of each element and/or compound and the density in the target object 3.

A method for determining the weight ratios of various elements and/or compounds and the density in the target object 3 is hereinafter described. The following description assumes that the target object 3 contains a plurality of elements, which are specifically five elements labeled a, b, c, d and e, and the kinds of these elements are known beforehand. As generally known, every element has an inherent absorption edge for X-rays. Meanwhile, as stated earlier, the energy range of X-rays generated by the X-ray source 1 is limited, and so is the energy range over which the X-ray detector 4 can detect X-rays. Therefore, it is possible that some of the five elements a to e have absorption edges within the measurable energy range while others do not. In the former case the contents of the elements can be determined using the absorption edges, whereas in the latter case the absorption edge cannot be used for contents determination. Accordingly, these two cases are hereinafter separately discussed.

[1] Using the Intensity Ratio Between the Transmitted and Direct X-Rays

In this case, a measured intensity of the direct X-ray is also utilized in addition to that of the transmitted X-ray. Therefore, measuring the direct X-ray is necessary. One method for measuring the direct X-ray is to dislocate the target object 3 in FIG. 1 before or after the measurement of the transmitted X-ray, in which case the direct X-ray can be detected by the same X-ray detector 4. Alternatively, another X-ray detector 4' capable of energy discrimination may be disposed at a position where the X-ray emitted from the X-ray source 1 can directly reach the X-ray detector 4' without passing through the target object 3. In this case, measuring the direct X-ray by the X-ray detector 4' can be concurrently performed with measuring the transmitted X-ray by the X-ray detector 4. However, as will be described later, the use of a two-dimensional detector in the present invention enables the measurement of the direct X-ray intensity by a different method that does not require dislocating the target object to directly measure the X-ray intensity or providing another X-ray detector.

Figure 2:
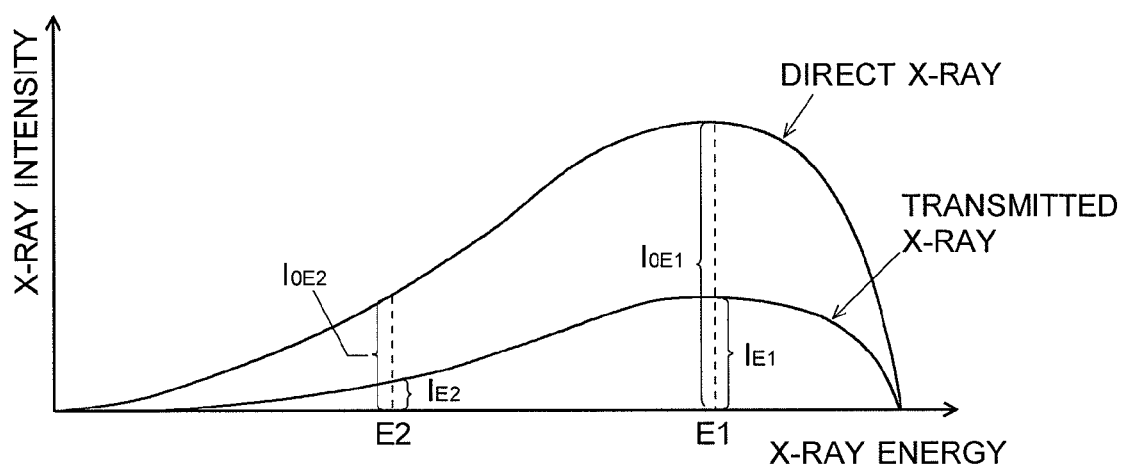
FIG. 2 is a graph showing an example of the energy spectrum in the case where none of the elements contained have an absorption edge.

FIG. 2 is a graph showing an example of the spectrums of the transmitted and direct X-rays. As shown, the X-ray undergoes absorption over the entire energy region when it passes through the target object 3, so that the intensity of the transmitted X-ray is lower than that of the direct X-ray. If the target object 3 contains more than one kind of element, i.e. if the target object 3 is a mixture or compound of a plurality of elements, the X-ray absorption will be the sum of absorptions by those elements. Therefore, by measuring the intensities of the direct X-ray (e.g. $I_{OE1}$ and $I_{OE2}$) and those of the transmitted X-ray (e.g. $I_{E1}$ and $I_{E2}$) at energy levels whose number is equal to or greater than that of the kinds of elements contained in the target object, it is possible to create the following system of equations from the ratio between the direct X-ray intensity and the transmitted X-ray intensity (e.g. $I_{OE1}/T_{E1}$) at each energy level and the theoretical ratio between the direct X-ray intensity and the transmitted X-ray intensity (this ratio can be calculated from the mass absorption coefficients of the elements concerned):

$$\ln(I_{OE1}/I_{E1}) = [(\mu/\rho)_{aE1} \cdot w_a + (\mu/\rho)_{bE1} \cdot w_b + \ldots + (\mu/\rho)_{eE1} \cdot w_e] \rho_m t_m \quad (1)$$

$$\ln(I_{OE2}/I_{E2}) = [(\mu/\rho)_{aE2} \cdot w_a \pm (\mu/\rho)_{bE2} \cdot w_b + \ldots + (\mu/\rho)_{eE2} \cdot w_e] \rho_m t_m \quad (2)$$

. . .

$$\ln(I_{OEn}/I_{En}) = [(\mu/\rho)_{aEn} \cdot w_a + (\mu/\rho)_{bEn} \cdot w_b + \ldots + (\mu/\rho)_{eEn} \cdot w_e] \rho_m t_m \quad (3)$$

Furthermore, the sum of the weight ratios of all the elements equals 1, so that:

$$w_a + w_b + \ldots + w_e = 1 \tag{4}$$

The parameters used in these equations are as follows:

$I_{0E1}$: Direct X-ray intensity at energy level E1
$I_{0E2}$: Direct X-ray intensity at energy level E2
$I_{0En}$: Direct X-ray intensity at energy level En (n is a value equal to or greater than the number of the kinds of elements contained in the target object)
$I_{E1}$: Transmitted X-ray intensity at energy level E1
$I_{E2}$: Transmitted X-ray intensity at energy level E2
$I_{En}$: Transmitted X-ray intensity at energy level En
$(\mu/\rho)_{aE1}$: Mass absorption coefficient of element a at energy level E1
$(\mu/\rho)_{bE1}$: Mass absorption coefficient of element b at energy level E1
$(\mu/\rho)_{eE1}$: Mass absorption coefficient of element e at energy level E1
$(\mu/\rho)_{aE2}$: Mass absorption coefficient of element a at energy level E2
$(\mu/\rho)_{bE2}$: Mass absorption coefficient of element b at energy level E2
$(\mu/\rho)_{eE2}$: Mass absorption coefficient of element e at energy level E2
$w_a$: Weight ratio of element a
$w_b$: Weight ratio of element b
$w_e$: Weight ratio of element e
$\rho_m$: Total density of the mixture (or compound)
$t_m$: Total thickness of the mixture (or compound)

In order to improve the measurement accuracy, the energy levels should not be close to each other.

If the target object contains a known kind of compound as well as individual elements, the previous method can be modified as follows. Imagine that the target object contains a known kind of compound "a" in place of, for example, the element "a." Knowing the kind of a compound means knowing the content percentage and density of each element contained in that compound. Accordingly, it is assumed that compound a consists of elements a1, a2 and a3 whose weights are respectively known as $w_{a1}$, $w_{a2}$ and $w_{a3}$. In this case, the weight ratios of compound a and other elements b, c, d and e and the entire density can be simultaneously determined by substituting the following equation into each of the equations (1) to (3):

$$(\mu/\rho)a = (\mu/\rho)w_{a1} + (\mu/\rho)w_{a2} + (\mu/\rho)w_{a3}$$

The density $\rho_a$, thickness $t_a$ and weight ratio $w_a$ of element a can be simply read as those of compound a. $(\mu/\rho)a$, $(\mu/\rho)w_{a1}$, $(\mu/\rho)w_{a2}$ and $(\mu/\rho)w_{a3}$ are as previously defined. Furthermore, the following equation holds true:

$$w_{a1} + W_{a2} + W_{a3} = 1$$

Then, the previous equations are rewritten by replacing the terms for element a with those for compound a. This rewriting does not require adding three equations for the three kinds of elements a1, a2 and a3 contained in compound a. Hence, there is no change in the number of energy levels and that of the equations. For example, the equation (1) can be rewritten as follows:

$$\ln(I_{0E1}/I_{E1}) = [\{(\mu/\rho)_{a1E1} \cdot w_{a1} + (\mu/\rho)_{a2E1} \cdot w_{a2} + (\mu/\rho)_{a3E1} \cdot w_{a3}\} \cdot w_a + (\mu/\sigma)_{bE1} \cdot w_b + \ldots + (\mu/\rho)_{eE1} \cdot w_e] \cdot \rho_m t_m$$

Equations (2) and (3) can also be similarly rewritten.

As already stated, some of the parameters in the aforementioned system of equations (e.g. the mass absorption coefficient of each element or constituent element at each energy level) are previously known and can be stored beforehand in a database or table created in a memory device. The intensities of the direct and transmitted X-rays at each energy level can be regarded as previously known since these values can be determined by actual measurements as explained earlier. The total thickness $t_m$ of the mixture (or compound) can also be separately determined by an actual measurement or other methods. Substituting these known values into the system of equations enables these equations to be solved for unknown values, such as the weight ratio of each element and/or compound and the density.

Figure 3:
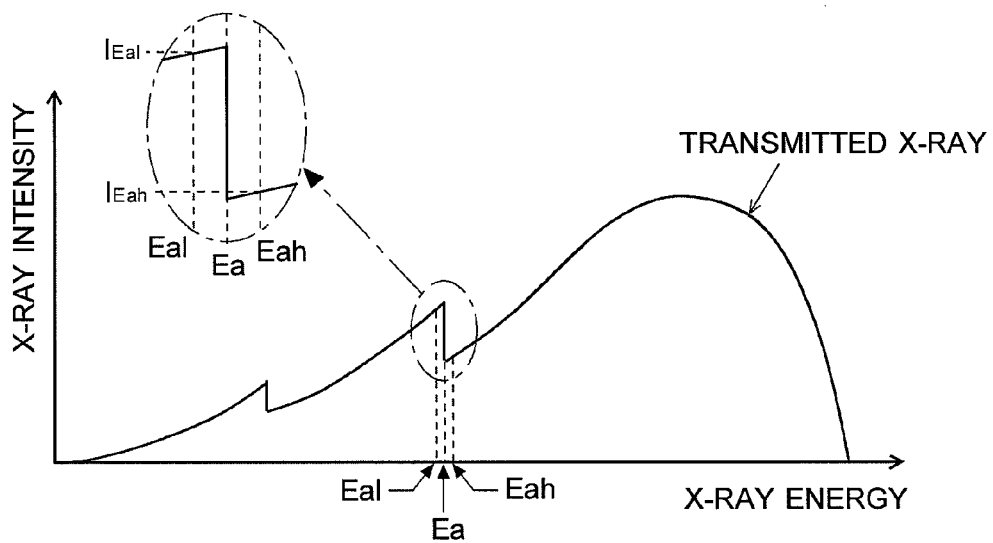
FIG. 3 is a graph showing an example of the energy spectrum in the case where all of the elements contained have absorption edges.

[2] Using the Intensity Ratio Between the Transmitted X-Rays Before and After the Absorption Edge Wavelength FIG. 3 is a graph showing an example of a transmitted X-ray spectrum of element a. As shown, the transmitted X-ray intensity suddenly changes before and after an energy level Ea corresponding to the absorption edge wavelength. Since the absorption edge wavelength is a unique property of each element, none of the elements b, c, d and e other than element a has an absorption edge at the energy level Ea. Therefore, using this intensity ratio makes it possible to measure a change in the weight ratio of element a with a high degree of sensitivity and accuracy.

Accordingly, for each of the elements a, b, . . . and e contained in the target object, the transmitted X-ray intensity is measured at an energy level slightly higher than the energy level of the absorption edge and also at a slightly lower energy level. For example, regarding element a, a transmitted X-ray intensity $I_{Eah}$ at an energy level Eah slightly higher than the energy level Ea corresponding to the absorption edge wavelength and a transmitted X-ray intensity $I_{Eal}$ at an energy level Eal slightly lower than the energy level Ea are determined, as shown in FIG. 3. From the ratio $I_{Eah}/I_{Eal}$ between the X-ray intensities before and after the energy level of the absorption edge of the element concerned, a theoretical intensity ratio of the transmitted X-ray that can be computed from the mass absorption coefficient of the element (and not its linear absorption coefficient), and a theoretical intensity ratio of the transmitted X-ray that can be computed from the mass absorption coefficient of each of the other coexisting elements at around the aforementioned absorption edge, it is possible to form the following system of equations. In these equations it is assumed that the direct X-ray intensity is constant and makes almost no change at energy levels around the absorption edge.

$$\ln(I_{Eah}/I_{Eal}) = [\{(\mu/\rho)_{aEal} - (\mu/\rho)_{aEah}\} \cdot w_a + \{(\mu/\rho)_{bEal} - (\mu/\rho)_{bEah}\} \cdot w_b + \ldots + \{(\mu/\rho)_{eEal} - (\mu/\rho)_{eEah}\} \cdot w_e] \cdot \rho_m t_m \tag{5}$$

$$\ln(I_{Ebh}/I_{Ebl}) = [\{(\mu/\rho)_{aEbl} - (\mu/\rho)_{aEbh}\} * w_a + \{(\mu/\rho)_{bEbl} - (\mu/\rho)_{bEbh}\} \cdot w_b + \ldots \{(\mu/\rho)_{eEel} - (\mu/\rho)_{eEeh}\} \cdot w_e] \cdot \rho_m t_m \tag{6}$$

. . .

$$\ln(I_{Eeh}/I_{Eel}) = [\{(\mu/\rho)_{aEel} - (\mu/\rho)_{aEeh}\} \cdot w_a + \{(\mu/\rho)_{bEel} - (\mu/\rho)_{bEeh}\} \cdot w_b + \ldots + (\mu/\rho)_{eEel} - (\mu/\rho)_{eEeh}\} \cdot w_e] \rho_m t_m \tag{7}$$

The parameters used in these equations are as follows:

$I_{Eah}$: Transmitted X-ray intensity at an energy level slightly higher than the energy level corresponding to the absorption edge wavelength of element a $I_{Ebh}$: Transmitted X-ray intensity at an energy level slightly higher than the energy level corresponding to the absorption edge wavelength of element b $I_{Eeh}$: Transmitted X-ray intensity at an energy level slightly higher than the energy level corresponding to the absorption edge wavelength of element e $I_{Eal}$: Transmitted X-ray intensity at an energy level slightly lower than the energy level corresponding to the absorption edge wavelength of element a $I_{Ebl}$: Transmitted X-ray intensity at an energy level slightly lower than the energy level corresponding to the absorption edge wavelength of element b $I_{Eel}$: Transmitted X-ray intensity at an energy level slightly lower than the energy level corresponding to the absorption edge wavelength of element e $(\mu/\rho)_{aEal}$: Mass absorption coefficient of element a at energy level Eal $(\mu/\rho)_{aEah}$: Mass absorption coefficient of element a at energy level Eah $(\mu/\rho)_{bEal}$: Mass absorption coefficient of element b at energy level Eal $(\mu/\rho)_{bEah}$: Mass absorption coefficient of element b at energy level Eah $(\mu/\rho)_{eEal}$: Mass absorption coefficient of element e at energy level Eal $(\mu/\rho)_{eEah}$: Mass absorption coefficient of element e at energy level Eah $(\mu/\rho)_{aEbl}$: Mass absorption coefficient of element a at energy level Ebl $(\mu/\rho)_{aEbh}$: Mass absorption coefficient of element a at energy level Ebh $(\mu/\rho)_{bEbl}$: Mass absorption coefficient of element b at energy level Ebl $(\mu/\rho)_{bEbh}$: Mass absorption coefficient of element b at energy level Ebh $(\mu/\rho)_{eEbl}$: Mass absorption coefficient of element e at energy level Ebl $(\mu/\rho)_{eEbh}$: Mass absorption coefficient of element e at energy level Ebh The equation (4) is also applicable to the present case.

If the target object 3 contains not only individual elements but also a known kind of compound, it is necessary to rewrite the equations by applying the same ideas as used in the previous case in which no absorption edge was used.

Among the parameters in the previously presented system of equations, the mass absorption coefficient of each of the elements a, b, ... and e (or the constituent elements a1, a2 and a3) at each energy level is previously known and can be stored beforehand in a database or table created in a memory device. The intensity ratio between the transmitted X-rays measured before and after the absorption edge of each of the elements a, b, ... and e (or each of the constituent elements a1, a2 and a3) $I_{Eah}/I_{Eal}$, $I_{Ebh}/I_{Ebl}$, ... $I_{Eeh}/I_{Eel}$, and so on can also be regarded as previously known since these values can be determined by actual measurements as explained earlier. The total thickness $t_m$ of the mixture (or compound) can also be separately determined by an actual measurement or other methods. Substituting these known values into the system of equations enables these equations to be solved for other unknown values, such as the weight ratios ($w_a$, $w_b$, ... $w_e$) of the elements and the total density ($\rho_m$).

[3] Using Both the Intensity Ratio Between the Transmitted X-Rays Before and After the Absorption Edge and the Intensity Ratio Between the Transmitted and Direct X-Rays If some of the elements contained in the target object have absorption edges within the available X-ray wavelength range while other elements do not, it is possible to create an equation based on the more accurate method [2] for each of the elements that have absorption edges and an equation based on the method [1] for each of the elements that do not have absorption edges. These equations can be combined to form a system of equations whose number is equal to or greater than the total number of elements and/or compounds having unknown weight ratios and the density, and this system of equations can be solved for unknown values, i.e. the weight ratio of each element and/or compound and the density.

As described thus far, the average weight ratios of known kinds of elements or compounds and the density in the target object 3 can be determined by any one of the methods [1], [2] and [3]. Even if any element or compound contained is unknown, the same method can be applied if its kind is presumable. Even if any element that is not actually contained has been presumed to be contained, its weight ratio will result in zero or a negligibly small value, so that no problem will arise. Conversely, if any element that is actually contained has not been presumed to be contained, an error will result. Although this problem can be avoided by including all of the elements that can possibly be contained, it should be noted that this approach requires an accordingly large number of equations and makes the process more complicated.

Figure 4:
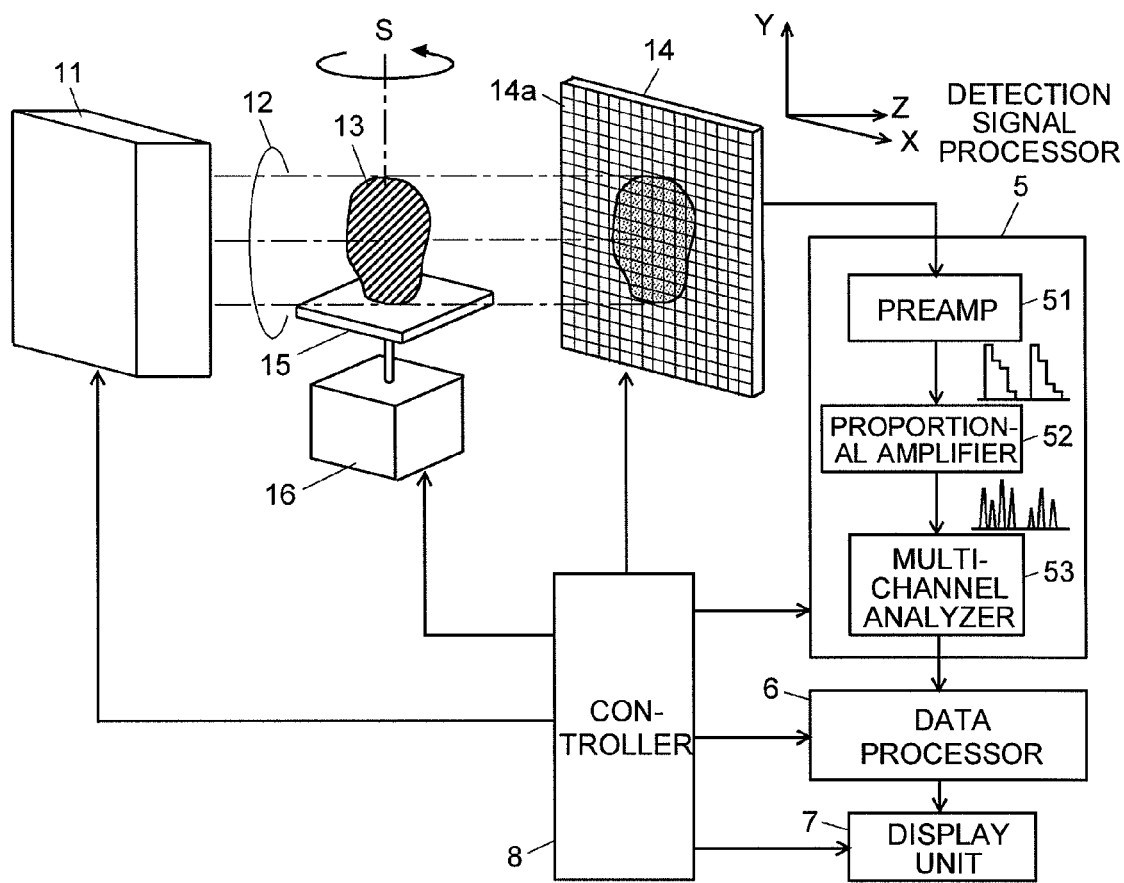
FIG. 4 is a schematic configuration diagram of an example of a transmitted X-ray measurement system used for carrying out the three-dimensional contents determination according to an embodiment of the present invention.

A three-dimensional contents determination method according to the present invention is hereinafter described. FIG. 4 is a schematic configuration diagram of an example of a transmitted X-ray measurement system used for carrying out the three-dimensional contents determination according to the present invention. The components which are identical or corresponding to those shown in FIG. 1 are denoted by the same numerals in order to clarify their correspondence.

In the transmitted X-ray measurement system of the present embodiment, parallel pencils of X-rays 12 emitted from a flat X-ray source 11 travel approximately parallel to the Z-axis and illuminate a three-dimensional target object 13. The X-rays pass through the target object 13, and the transmitted X-rays impinge on a two-dimensional X-ray detector 14 having a flat detection surface. The two-dimensional X-ray detector 14 is a two-dimensional array of a large number of micro-sized X-ray detection elements 14a arranged in horizontal and vertical directions (along the X and Y axes), with each element 14a being capable of directly detecting X-rays within a predetermined wavelength range. For example, a CCD detector including CCD elements capable of directly detecting X-rays may be used. The X-ray source 11 is similar to the previous X-ray source 1 and capable of generating X-rays over a predetermined energy range and not at one specific wavelength (i.e. not at a specific energy level).

In the two-dimensional X-ray detector 14, each micro-sized X-ray detection element that has received a transmitted or direct X-ray generates an electric signal corresponding to the wavelength (i.e. energy) of the X-ray. With regards to the transmitted X-ray, the detection signal generated by a micro-sized X-ray detection element 14a at a different position on the detection surface of the two-dimensional X-ray detector 14 contains information about the elements located at a different position in the target object 13. Accordingly, the detection signal processor 5 sends the data processor 6 a value corresponding to the intensity of the transmitted or direct X-ray received by each micro-sized X-ray detection element 14a of the two-dimensional X-ray detector 14.

Under the control of the controller 8, the target object 13 placed on the sample stage 15 is rotationally scanned by the scan rotation drive 16 in steps of a predetermined angle θ around the axis S perpendicular to the incident X-ray. Instead of rotating the target object 13 as in this example, the system may statically hold the target object 13 and rotate the pair of the X-ray source 11 and two-dimensional X-ray detector 14 facing each other across the target object 13 around the axis S.

In summary, the previously described system can measure the intensity of the transmitted or direct X-ray received by each micro-sized X-ray detection element 14a of the two-dimensional X-ray detector 14 when the target object 13 is held at a specific rotation angle. While rotationally scanning the target object 13, the system measures the two-dimensional intensities of the transmitted and direct X-rays. The X-ray intensity data thus obtained is sent to the data processor 6, which performs calculations with the intensity data, as will be described later, to obtain information about a three-dimensional distribution of the elements and/or compounds contained in the target object 13. The information thereby obtained is shown on the display unit 7.

The previously described basic idea is also applicable to the present case. That is to say, a system of equations is formed using unknown values (e.g. the weight ratio of each element and/or compound and the density in the target object 13) and known values (e.g. actual intensity data of the transmitted and direct X-rays and the mass absorption coefficient of each element), and then solved for the weight ratio of each element and/or compound and the density. However, the method in the present case is further sophisticated for the purpose of obtaining three-dimensional distribution information. This method is hereinafter described with reference to FIGS. 5 and 6 in addition to FIG. 4.

Figure 5:
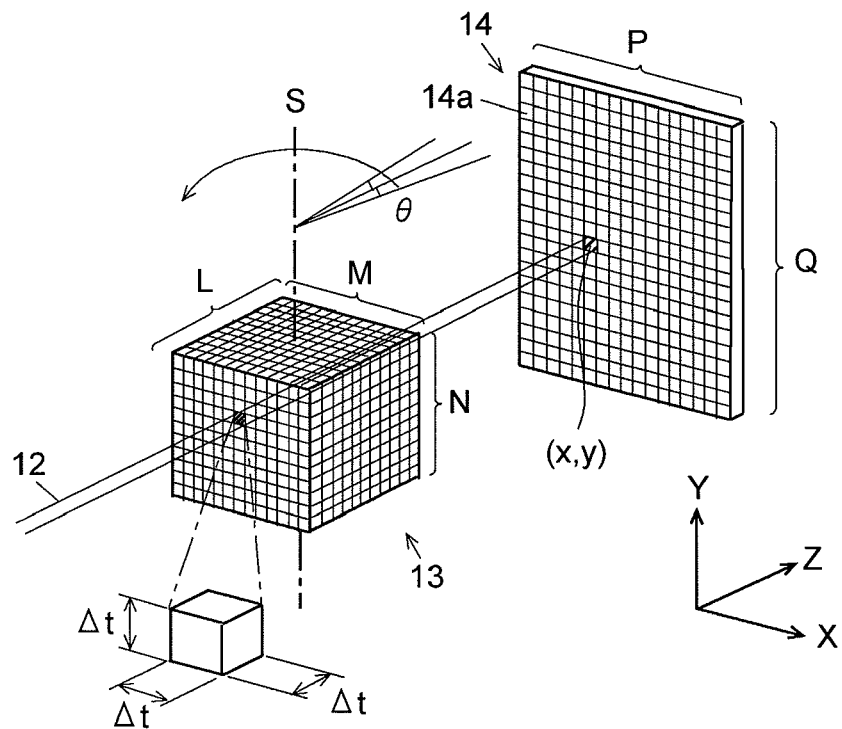
FIG. 5 is a model diagram for illustrating a three-dimensional contents determination method according to the embodiment shown in FIG. 5.
Figure 6:
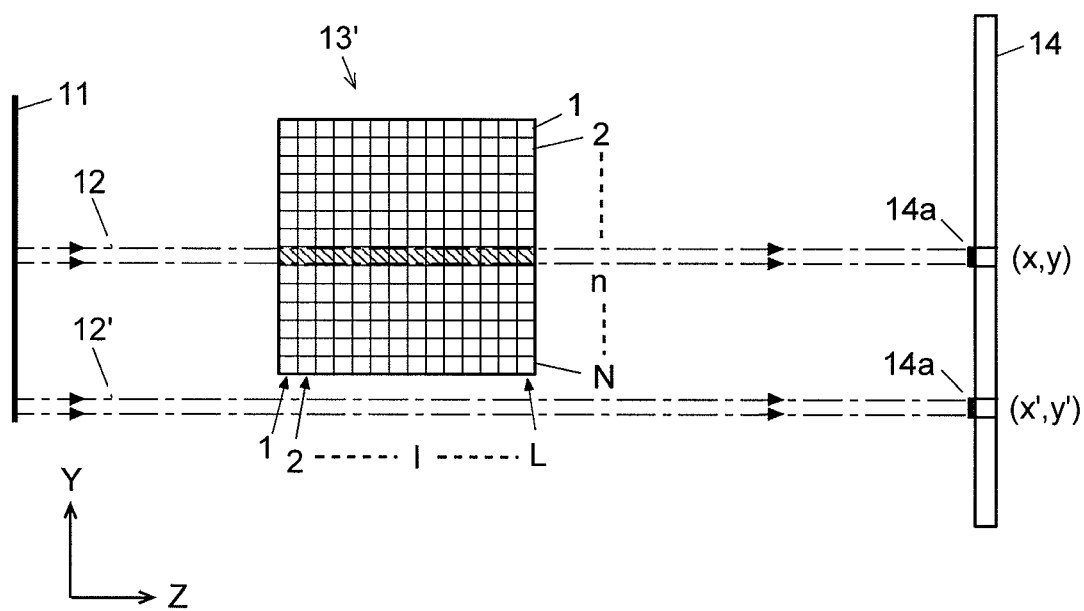
FIG. 6 is a model diagram for illustrating the three-dimensional contents determination method according to the embodiment.

In this method, a micro-sized unitary cubic cell (a cube with a side length $\Delta t$) is defined within the target object 13, taking into account the relationship between the illumination area of the incident X-ray on the target object 13 and the passage area of the exit X-ray, the size of the light-receiving surface of a single micro-sized X-ray detection element 14a of the two-dimensional X-ray detector 14, the scan rotation angle $\theta$, and so on. Then, it is assumed that the target object 13 consists of a large number of unitary cubic cells, with L pieces aligned along the Z-axis, N pieces along the Y-axis and M pieces along the X-axis. Since the incident X-ray in this example is the parallel pencils of X-rays 12, the illumination area of the incident X-ray equals the passage area of the exit X-ray. Therefore, it is possible to imagine a modeled target object 13' as shown in FIGS. 5 and 6. FIG. 6 is a sectional view at a Y-Z plane in which the parallel pencils of X-rays 12 are passing in FIG. 5.

As shown in FIG. 6, this state can be interpreted as follows. An X-ray passes through a plurality of unitary cubic cells aligned along the Z-axis inside the modeled target object 13', and the transmitted X-ray impinges on the light-receiving surface of a micro-sized X-ray detection element 14a at a position (x, y) on the two-dimensional X-ray detector 14 having P×Q pieces of micro-sized light-receiving elements 14a. This transmitted X-ray is an X-ray that has undergone absorptions by the elements and/or compounds contained in each of the plurality of unitary cubic cells. Meanwhile, this modeled target object 13' is rotated around the S axis in steps of a predetermined scan rotation angle $\theta$. This causes a change in the combination of the unitary cubic cells which the X-ray passes through before it reaches the two-dimensional X-ray detector 14. For every rotation of the target object 13' by the predetermined scan rotation angle $\theta$, the X-ray is detected by each micro-sized X-ray detection element 14a. Subsequently, the detection signal processor 5 determines the X-ray intensity at each of the energy levels E1 and E2.

The contents determination method can be selected from the previously described three methods [1], [2] and [3]. Initially, case [1] is considered, where the intensity ratio between the transmitted and direct X-rays is used.

As shown in FIG. 6, consider the situation where an X-ray passes through L pieces of unitary cubic cells (1, m, n), (2, m, n), ... and (L, m, n) within the target object 13' and is detected by a micro-sized X-ray detection element 14a located at (x, y). The direct X-ray intensity can be measured by the same micro-sized X-ray detection element 14a as used in the measurement of the transmitted X-ray when the target object 13 is not present between the X-ray source 11 and two-dimensional X-ray detector 14. However, if, as shown in FIG. 6, there is a parallel pencil of incident X-rays 12' directly impinging on some of the micro-sized X-ray detection elements on the detection surface of the X-ray detection detector 14 without being blocked by the target object 13', it is possible to simultaneously measure the direct X-ray intensity and the transmitted X-ray intensity; the direct X-ray can be detected by a micro-sized X-ray detection element 14a located at any position (x', y') where the X-ray is directly coming.

If X-rays are emitted from the same X-ray source 11 and travel the same distance, all of the pencils of incident X-rays can be regarded as identical in energy distribution since the only difference is whether or not the X-ray passes through the target object 13. If the micro-sized X-ray detection elements 14a are at different distances from the X-ray source 11, these differences can be corrected so that the direct X-ray intensity measured by the micro-sized X-ray detection element 14a at the aforementioned position (x', y') will be applicable to all of the other micro-sized X-ray detection elements 14a within the area where the transmitted X-ray is detected by the two-dimensional X-ray detector 14. The direct X-ray intensity thus detected by the micro-sized X-ray detection element 14a at the position (x', y') is applicable to any scan rotation angle since the positional relationship between the X-ray source 11 and two-dimensional X-ray detector 14 is unaffected by the angle. Accordingly, the direct X-ray intensity needs to be measured only once at one specific angle.

In the present case, the following system of equations with four variables can be created at X-ray energy levels E1 and E2, using the measured intensity ratio between the direct and transmitted X-rays and a theoretical intensity ratio calculated from the mass absorption coefficients (known) and weight ratios (unknown) of the elements and/or compounds and their density (unknown) in each of the L pieces of unitary cubic cells which the X-ray passes through:

$$\ln(I_{0,x,y,\theta 1,E1}/I_{x,y,\theta 1,E1}) = \{(\mu/\rho)_{aE1} \cdot w_{a,1,m,n} + (\mu/\rho)_{bE1} \cdot w_{b,1,m,n} + \ldots\} \cdot \rho_{1,m,n} \cdot \Delta t + \{(\mu/\rho)_{aE1} \cdot w_{a,2,m,n} + (\mu/\rho)_{bE1} \cdot w_{b,2,m,n} + \ldots\} \cdot \rho_{2,m,n} \cdot \Delta t + \{(\mu/\rho)_{aE1} \cdot w_{a,3,m,n} + (\mu/\rho)_{bE1} \cdot w_{b,3,m,n} + \ldots\} \cdot \rho_{3,m,n} \cdot \Delta t + \ldots + \{(\mu/\rho)_{aE1} \cdot w_{a,L,m,n} + (\mu/\rho)_{bE1} \cdot w_{b,L,m,n} + \ldots\} \cdot \rho_{L,m,n} \cdot \Delta t \quad (8)$$

$$\ln(I_{0,x,y,\theta 1,E2}/I_{x,y,\theta 1,E2}) = \{(\mu/\rho)_{aE2} \cdot w_{a,1,m,n} + (\mu/\rho)_{bE2} \cdot w_{b,1,m,n} + \ldots\} \cdot \rho_{1,m,n} \cdot \Delta t + \{(\mu/\rho)_{aE2} \cdot w_{a,2,m,n} + (\mu/\rho)_{bE2} \cdot w_{b,2,m,n} + \ldots\} \cdot \rho_{2,m,n} \cdot \Delta t + \{(\mu/\rho)_{aE2} \cdot w_{a,3,m,n} + (\mu/\rho)_{bE2} \cdot w_{b,3,m,n} + \ldots\} \cdot \rho_{3,m,n} \cdot \Delta t + \ldots + \{(\mu/\rho)_{aE2} \cdot w_{a,L,m,n} + (\mu/\rho)_{bE2} \cdot w_{b,L,m,n} + \ldots\} \cdot \rho_{L,m,n} \cdot \Delta t \quad (9)$$

In these equations:

$I_{0,x,y,\theta 1,E1}$ is a direct X-ray intensity measured at the energy level E1 and a scan angle position $\theta 1$ by a micro-sized X-ray detection element located at (x, y), $I_{x,y,\theta 1,E1}$ is a transmitted X-ray intensity measured at the energy level E1 and a scan angle position $\theta 1$ by a micro-sized X-ray detection element located at (x, y), $I_{0,x,y,\theta 1,E2}$ is a direct X-ray intensity measured at the energy level E2 and a scan angle position $\theta 1$ by a micro-sized X-ray detection element located at (x, y), and $I_{x,y,\theta1,E2}$ is a transmitted X-ray intensity measured at the energy level E2 and a scan angle position θ1 by a micro-sized X-ray detection element located at (x, y).

The equations (8) and (9) are a system of equations with four variables x=1 to P, y=1 to Q, θ=θ1 to θr, and E=E1 to Eu. The unknown values are $w_{a,l,m,n}, w_{b,l,m,n}, \ldots$ and $\rho_{l,m,n}$ (l=1 to L, m=1 to M and n=1 to N), where:

$w_{a,l,m,n}$ is the weight ratio of element a contained in the unitary cubic cell (l, m, n) of the target object 13', $w_{b,l,m,n}$ is the weight ratio of element b contained in the unitary cubic cell (l, m, n) of the target object 13', and $\rho_{l,m,n}$ is the density of the target object 13' within the unitary cubic cell (l, m, n). In addition, the following equation holds true since the sum of the weight ratios of the elements and/or compounds contained in each unitary cubic cell equals one:

$$w_{a,l,m,n} + w_{b,l,m,n} + \ldots = 1 \quad (10)$$

Accordingly, what is required to be done in this instance is to combine the equations (8), (9) and (10) to create a system of equations whose number is equal to or greater than the sum of the total number (T) of elements and/or compounds contained in each unitary cubic cell and the density, i.e. L×M×N×T. Specifically, the number of equations can be expressed as r×(P×Q)×u+(L×M×N), where r is the repetition number of the scan operation by the predetermined scan rotation angle θ, (P×Q) is the total number of micro-sized X-ray detection elements 14a of the two-dimensional X-ray detector 14, and u is the number of energy levels (E1, E2, ... ). Therefore, the aforementioned requirement can be expressed as r×(P×Q)×u+(L×M×N)≧L×M×N×T. These calculations are performed by the data processor 6. Simultaneously, a coordinate transformation is performed for determining the relationship between the array of the unitary cubic cells in the target object 13' at an initial rotational position and a plurality of unitary cubic cells which the incident X-ray passes through at a given rotational scan position so as to create the equations (8) and (9) for that position. The system of equations thus created can be solved for the weight ratios of the elements and/or compounds and their density in each unitary cubic cell by a least-square method or other numerical calculations.

Next, case [2] is considered, where the intensity ratio between the transmitted X-rays before and after the absorption edge wavelength is used. In this case, a different system of equations is required since the direct X-ray is not measured in case [2]; instead, the equations utilize the transmitted X-ray intensities measured at energy levels slightly higher and lower than the absorption edge of each element. As shown in FIG. 6, consider once more the situation where an X-ray passes through L pieces of unitary cubic cells (1, m, n), (2, m, n), ... and (L, m, n) within the target object 13' and is detected by a micro-sized X-ray detection element 14a located at (x, y). In this case, a system of equations with four variables can be created as follows, using an actual intensity ratio between the transmitted X-rays measured at energy levels slightly higher and lower than the absorption edge and a theoretical intensity ratio calculated from the mass absorption coefficients (known) and weight ratios (unknown) of the elements and/or compounds and their density (unknown) in each of the L pieces of unitary cubic cells which the X-ray passes through:

$$\ln(I_{x,y,\theta1,Eah}/I_{x,y,\theta1,Eal}) = [\{(\mu/\rho)_{aEal} - (\mu/\rho)_{aEah}\} \cdot w_{a,1,m,n} + \{(\mu/\rho)_{bEal} - (\mu/\rho)_{bEah}\} \cdot w_{b,1,m,n} + \ldots + \{(\mu/\rho)_{eEal} - (\mu/\rho)_{eEah}\} \cdot w_{e,1,m,n}] \cdot \rho_{1,m,n} \cdot \Delta t + [\{(\mu/\rho)_{aEal} - (\mu/\rho)_{aEah}\} \cdot w_{a,2,m,n} + \{(\mu/\rho)_{bEal} - (\mu/\rho)_{bEah}\} \cdot w_{b,2,m,n} + \ldots + \{(\mu/\rho)_{eEal} - (\mu/\rho)_{eEah}\} \cdot w_{e,2,m,n}] \rho_{2,m,n} \cdot \Delta t + \ldots + [\{(\mu/\rho)_{aEal} - (\mu/\rho)_{aEah}\} \cdot w_{a,L,m,n} + \{(\mu/\rho)_{bEal} - (\mu/\rho)_{bEah}\} \cdot w_{b,L,m,n} + \ldots + \{(\mu/\rho)_{eEal} - (\mu/\rho)_{eEah}\} \cdot w_{e,L,m,n}] \cdot \rho_{L,m,n} \cdot \Delta t \quad (11)$$

$$\ln(I_{x,y,\theta1,Ebh}/I_{x,y,\theta1,Ebl}) = [\{(\mu/\rho)_{aEbl} - (\mu/\rho)_{aEbh}\} \cdot w_{a,1,m,n} + \{(\mu/\rho)_{bEbl} - (\mu/\rho)_{bEbh}\} \cdot w_{b,1,m,n} + \ldots + \{(\mu/\rho)_{eEbl} - (\mu/\rho)_{eEbh}\} \cdot w_{e,1,m,n}] \cdot \rho_{1,m,n} \cdot \Delta t + [\{(\mu/\rho)_{aEbl} - (\mu/\rho)_{aEbh}\} \cdot w_{a,2,m,n} + \{(\mu/\rho)_{bEbl} - (\mu/\rho)_{bEbh}\} \cdot w_{b,2,m,n} + \ldots + \{(\mu/\rho)_{eEbl} - (\mu/\rho)_{eEbh}\} \cdot w_{e,2,m,n}] \rho_{2,m,n} \cdot \Delta t + \ldots + [\{(\mu/\rho)_{aEbl} - (\mu/\rho)_{aEbh}\} \cdot w_{a,L,m,n} + \{(\mu/\rho)_{bEbl} - (\mu/\rho)_{bEbh}\} \cdot W_{b,L,m,n} + \ldots + \{(\mu/\rho)_{eEbl} - (\mu/\rho)_{eEbh}\} \cdot w_{e,L,m,n}] \cdot \rho_{L,m,n} \cdot \Delta t \quad (12)$$

In these equations:

$I_{x,y,\theta1,Eah}$ is a transmitted X-ray intensity measured at an energy level Eah slightly higher than the absorption edge of element a, and at a scan angle position θ1 by a micro-sized X-ray detection element located at (x, y), $I_{x,y,\theta1,Eal}$ is a transmitted X-ray intensity measured at an energy level Eal slightly lower than the absorption edge of element a, and at a scan angle position θ1 by a micro-sized X-ray detection element located at (x, y), $I_{x,y,\theta1,Ebh}$ is a transmitted X-ray intensity measured at an energy level Ebh slightly higher than the absorption edge of element b, and at a scan angle position θ1 by a micro-sized X-ray detection element located at (x, y), and $I_{x,y,\theta1,Ebl}$ is a transmitted X-ray intensity measured at an energy level Ebl slightly lower than the absorption edge of element b, and at a scan angle position θ1 by a micro-sized X-ray detection element located at (x, y).

The equations (11) and (12) are a system of equations with four variables x=1 to P, y=1 to Q, θ=θ1 to θr, and E=(Eah, Eal), (Ebh, Ebl) and so on. As in the preceding case, the unknown values are $w_{a,l,m,n}, w_{b,l,m,n}, \ldots$ and $\rho_{l,m,n}$ (l=1 to L, m=1 to M and n=1 to N). Although the contents of this system of equations differ from those of the previous case, these equations can be solved in the same manner, i.e. by creating a predetermined number of equations to form a system of equations and solving them for the weight ratios of the elements and/or compounds and their density in each unitary cubic cell.

Next, case [3] is considered, where both the intensity ratio between the transmitted X-rays before and after the absorption edge and the intensity ratio between the transmitted and direct X-rays are used. In case [3], some of the elements contained in the target object have absorption edges while others do not. In such a case, a system of equations with four variables x=1 to P, y=1 to Q, θ=θ1 to θr and E=(Eah, Eal), (Ebh, Ebl) ... can be formed by creating an equation similar to the highly accurate equation (11) for each of the elements having the absorption edge within the available X-ray wavelength range and an equation similar to the equation (8) for each of the elements that do not have absorption edges within that range. As in the two preceding cases, the unknown values are $w_{a,l,m,n}, w_{b,l,m,n}, \ldots$ and (l=1 to L, m=1 to M and n=1 to N). Although the system of equations in the present case includes two types of equations, they can be solved in the same manner, i.e. by creating a predetermined number of equations to form a system of equations and solving them for the weight ratios of the elements and/or compounds and their density in each unitary cubic cell.

Figure 7:
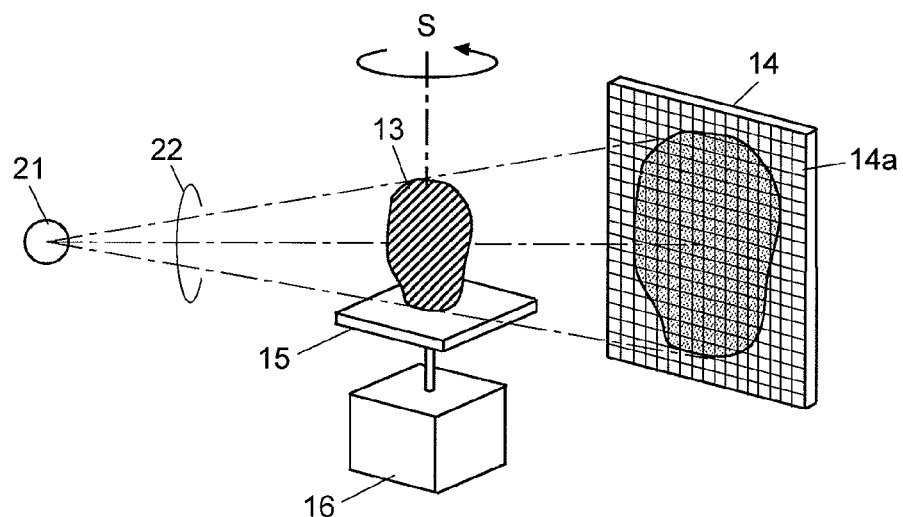
FIG. 7 is a schematic configuration diagram of an example of a transmitted X-ray measurement system used for carrying out a three-dimensional contents determination according to another embodiment of the present invention.
Figure 8:
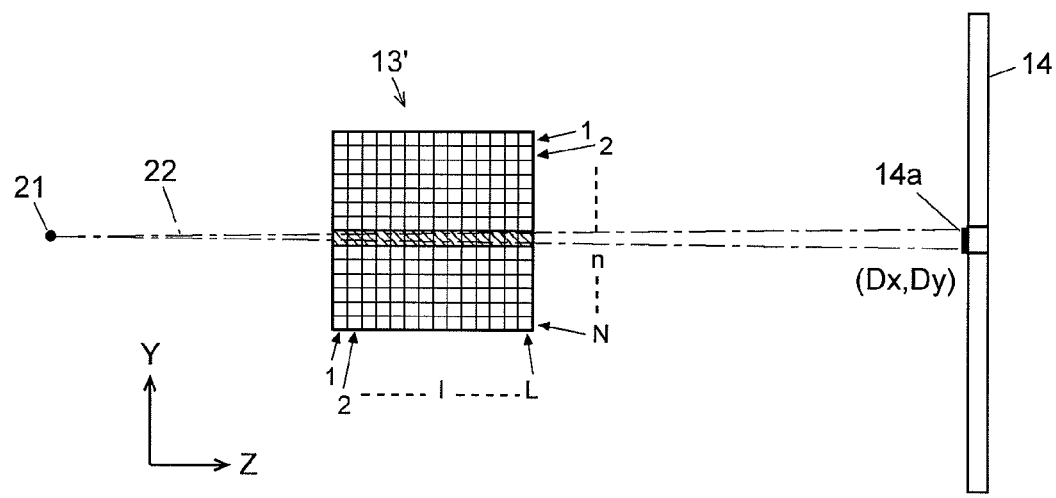
FIG. 8 is a model diagram illustrating the three-dimensional contents determination method according to the embodiment shown in FIG. 7.

The previous embodiment assumed that the X-ray impinging on the target object was parallel pencils of X-rays. This configuration can be changed as shown in FIG. 7, in which the target object 13 is irradiated with a divergent X-ray 22 spreading from an X-ray source 21 that can be practically regarded as a point source of light, and the transmitted X-ray is detected by the two-dimensional X-ray detector 14. However, there are some differences to be considered. Firstly, unlike the previous embodiment in which a real-sized X-ray image of the target object 13 was projected on the detection surface of the two-dimensional X-ray detector 14, in the present case the X-ray image projected on the detection surface of the two-dimensional X-ray detector 14 is an enlarged image of the target object 13 since the divergent X-ray 22 is used. Secondly, when determining the size of the unitary cubic cell, it is necessary to take into account the spread of the X-ray within the target object 13 because, as shown in FIG. 8 which corresponds to FIG. 6, the illumination area of the incident X-ray on the target object 13 differs from the exit area of the X-ray. Finally, the array (or combination) of unitary cubic cells which the X-ray passes through differs from that of the previous embodiment since the incident X-ray falling onto the target object 13 in the present case is not always perpendicular to the rotation axis S. These factors must be considered in the coordinate transformation, so that the calculations are more complicated than in the previous embodiment. However, the basic idea for the three-dimensional contents determination in the previous embodiment is still applicable.

It should be noted that the previous embodiments are mere examples, and any changes, modifications or additions that are appropriately made within the spirit of the present invention will evidently be included in the scope of the claims of this patent application.

The invention claimed is:

1. A three-dimensional contents determination method using a transmitted X-ray, for determining a three-dimensional distribution of weight ratios and density of elements and/or compounds contained in a target object by means of an X-ray measurement system including:

an X-ray irradiator for irradiating the target object with a divergent X-ray or parallel pencils of X-rays having a predetermined energy range;

an X-ray detector with a two-dimensional array of micro-sized X-ray detection elements capable of energy discrimination for detecting a transmitted X-ray that has passed through the target object or a direct X-ray that has not passed through the target object;

a signal processor for obtaining X-ray intensity data of the transmitted or direct X-ray for each of the micro-sized X-ray detection elements on a basis of a detection signal produced by the X-ray detector; and a rotational scanner for rotating either the target object or the X-ray irradiator and the X-ray detector in steps of a predetermined rotation angle so that a relative position of the target object, the X-ray irradiator and the X-ray detector changes around an axis perpendicularly or obliquely intersecting with an incident X-ray impinging on the target object, the contents determination method comprising steps of:

imaginarily dividing the target object into a large number of three-dimensionally arranged unitary cubic cells, a size of the unitary cubic cell being determined by taking into account a difference between an incident area and exit area of the X-ray passing through the target object, a size of a detection surface of the micro-sized X-ray detection element, and a scan angle of the rotational scanner;

creating, for each rotational scan operation and each micro-sized X-ray detection element, a system of equations whose number is equal to or greater than a total number of elements and/or compounds having unknown weight ratios and the density in each of the aforementioned one or more unitary cubic cells including an equation including a measured intensity ratio between an intensity of the transmitted X-ray that has passed through the target object and an intensity of the direct X-ray that has not passed through the target object at a same energy level and a theoretical X-ray intensity ratio expressed using the mass absorption coefficients, the weight ratios and the density of all the elements and/or compounds contained in one or more unitary cubic cells located within a range where the X-ray passes through the target object, and an equation expressing that a sum of the weight ratios of the elements and/or compounds contained in one or more unitary cubic cells located within a range where the X-ray passes through the target object equals one; and detecting the transmitted X-ray that has passed through the target object and the direct X-ray that has not passed therethrough by means of the X-ray detector, calculating the measured intensity ratio from the X-ray intensity data thereby obtained, applying the measured intensity ratio to the system of equations, and solving the system of equations for the weight ratio of each element and/or compound and the density in each unitary cubic cell, thereby determining the three-dimensional distribution of the elements and/or compounds contained in the target object.

2. A three-dimensional contents determination method using a transmitted X-ray, for determining a three-dimensional distribution of weight ratios and density of elements and/or compounds contained in a target object by means of an X-ray measurement system including:

an X-ray irradiator for irradiating the target object with a divergent X-ray or parallel pencils of X-rays having a predetermined energy range;

an X-ray detector with a two-dimensional array of micro-sized X-ray detection elements capable of energy discrimination for detecting a transmitted X-ray that has passed through the target object;

a signal processor for obtaining X-ray intensity data of the transmitted X-ray for each of the micro-sized X-ray detection elements on a basis of a detection signal produced by the X-ray detector; and a rotational scanner for rotating either the target object or the X-ray irradiator and the X-ray detector in steps of a predetermined rotation angle so that a relative position of the target object, the X-ray irradiator and the X-ray detector changes around an axis perpendicularly or obliquely intersecting with an incident X-ray impinging on the target object, the contents determination method comprising steps of:

imaginarily dividing the target object into a large number of three-dimensionally arranged unitary cubic cells, a size of the unitary cubic cell being determined by taking into account a difference between an incident area and exit area of the X-ray passing through the target object, a size of a detection surface of the micro-sized X-ray detection element, and a scan angle of the rotational scanner;

in a case where all of the elements and/or the constituent elements of all of the compounds contained in the target object have absorption edges within an energy range that is measurable for a combination of the X-ray irradiator and the X-ray detector, creating, for each rotational scan operation and each micro-sized X-ray detection element, a system of equations whose number is equal to or greater than a total number of elements and/or compounds having unknown weight ratios and the density in each of the aforementioned one or more unitary cubic cells including an equation including a transmitted X-ray intensity ratio measured on both sides of the absorption edge of each element and a theoretical X-ray intensity ratio expressed using the mass absorption coefficients, the weight ratios and the density of all the elements and/or compounds contained in one or more unitary cubic cells located within a range where the X-ray passes through the target object, and an equation expressing that a sum of the weight ratios of the elements and/or compounds contained in one or more unitary cubic cells located within a range where the X-ray passes through the target object equals one; and detecting the transmitted X-ray that has passed through the target object by means of the X-ray detector, calculating the transmitted X-ray intensity ratio from the X-ray intensity data thereby obtained, applying the transmitted X-ray intensity ratio to the system of equations, and solving the system of equations for the weight ratio of each element and/or compound and the density in each unitary cubic cell, thereby determining the three-dimensional distribution of the elements and/or compounds contained in the target object.

3. A three-dimensional contents determination method using a transmitted X-ray, for determining a three-dimensional distribution of weight ratios and density of elements and/or compounds contained in a target object by means of an X-ray measurement system including:

an X-ray irradiator for irradiating the target object with a divergent X-ray or parallel pencils of X-rays having a predetermined energy range;

an X-ray detector with a two-dimensional array of micro-sized X-ray detection elements capable of energy discrimination for detecting a transmitted X-ray that has passed through the target object or a direct X-ray that has not passed through the target object;

a signal processor for obtaining X-ray intensity data of the transmitted or direct X-ray for each of the micro-sized X-ray detection elements on a basis of a detection signal produced by the X-ray detector; and a rotational scanner for rotating either the target object or the X-ray irradiator and the X-ray detector in steps of a predetermined rotation angle so that a relative position of the target object, the X-ray irradiator and the X-ray detector changes around an axis perpendicularly or obliquely intersecting with an incident X-ray impinging on the target object, the contents determination method comprising steps of:

imaginarily dividing the target object into a large number of three-dimensionally arranged unitary cubic cells, a size of the unitary cubic cell being determined by taking into account a difference between an incident area and exit area of the X-ray passing through the target object, a size of a detection surface of the micro-sized X-ray detection element, and a scan angle of the rotational scanner;

for each of the elements and/or compounds contained in the target object, if the element has an absorption edge within an energy range that is measurable for a combination of the X-ray irradiator and the X-ray detector, then, creating, for each rotational scan operation and each micro-sized X-ray detection element, a system of equations whose number is equal to or greater than a total number of elements and/or compounds having unknown weight ratios and the density in each of the aforementioned one or more unitary cubic cells including an equation including a transmitted X-ray intensity ratio measured on both sides of the absorption edge of each element and a theoretical X-ray intensity ratio expressed using the mass absorption coefficients, the weight ratios and the density of all the elements contained in one or more unitary cubic cells located within a range where the X-ray passes through the target object, and an equation expressing that a sum of the weight ratios of the elements and/or compounds contained in one or more unitary cubic cells located within a range where the X-ray passes through the target object equals one;

if the each element has no absorption edge within the measurable energy range, then, creating a system of equations whose number is equal to or greater than a total number of elements and/or compounds having unknown weight ratios and the density in each of the aforementioned one or more unitary cubic cells including an equation including a measured intensity ratio between an intensity of the transmitted X-ray that has passed through the target object and an intensity of the direct X-ray that has not passed through the target object at the same energy level, and a theoretical X-ray intensity ratio expressed using the mass absorption coefficients, the weight ratios and the density of all the elements contained in one or more unitary cubic cells located within a range where the X-ray passes through the target object, and an equation expressing that a sum of the weight ratios of the elements and/or compounds contained in one or more unitary cubic cells located within a range where the X-ray passes through the target object equals one; and detecting the transmitted X-ray that has passed through the target object by means of the X-ray detector, and also detecting the direct X-ray that has not passed through the target object by means of the X-ray detector, and calculating the transmitted X-ray intensity ratio or measured intensity ratio from the X-ray intensity data thereby obtained, applying the transmitted X-ray intensity ratio or measured intensity ratio to the system of equations, and solving the system of equations for the weight ratio of each element and/or compound and the density in each unitary cubic cell, thereby determining the three-dimensional distribution of the elements and/or compounds contained in the target object.

4. The three-dimensional contents determination method according to claim 1, wherein:

parallel pencils of X-rays are used as the X-ray; and if a parallel pencil of incident X-rays is directly impinging on some of the micro-sized X-ray detection elements of the X-ray detection detector without being blocked by the target object, the intensity of the direct X-ray is measured by a micro-sized X-ray detection element located at any position where the X-ray is directly coming.

5. The three-dimensional contents determination method according to claim 3, wherein:
   parallel pencils of X-rays are used as the X-ray; and
   if a parallel pencil of incident X-rays is directly impinging on some of the micro-sized X-ray detection elements of the X-ray detection detector without being blocked by the target object, the intensity of the direct X-ray is measured by a micro-sized X-ray detection element located at any position where the X-ray is directly coming.

* * * * *